United States Patent

Harsanyi et al.

Patent Number: 5,162,359
Date of Patent: Nov. 10, 1992

[54] ANTIHYPERLIPOPROTEINEMIC 5-BENZYL SUBSTITUTED-BENZIMIDAZOLINE-2-THION DERIVATIVES

[75] Inventors: Kálmán Harsanyi; Péter Tétényi; Tamás Nagy, all of Budapest; Attila Csehi, Göd; Tibor Gizur, Budapest; Béla Hegedüs, Budapest; Andrea Maderspach, Budapest; András Jávor, Budapest; György Hajós, Budapest; László Szporny, Budapest, all of Hungary

[73] Assignee: Richter Gedeon Vegyeszeti Gyar Rt., Budapest, Hungary

[21] Appl. No.: 753,751

[22] Filed: Sep. 3, 1991

[30] Foreign Application Priority Data

Sep. 3, 1990 [HU] Hungary .................. 5746/90

[51] Int. Cl.⁵ .................. A61L 31/415; C07D 235/28
[52] U.S. Cl. .................. 514/387; 548/307.1
[58] Field of Search .................. 548/305; 514/387

[56] References Cited

U.S. PATENT DOCUMENTS 4,814,329 3/1989 Harsanyi et al. .................. 514/211

Primary Examiner—Patricia L. Morris
Attorney, Agent, or Firm—Herbert Dubno; Jonathan Myers

[57] ABSTRACT

Novel antihyperlipoproteinemic compounds are disclosed of the formula I,

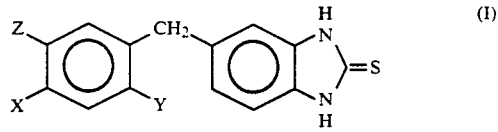

wherein
X is a halogen atom, methyl, ethyl, methoxy or ethoxy group,
Y is hydroxy if X is methoxy or ethoxy, otherwise it is a hydrogen atom or a, methoxy or ethoxy group,
Z is a methoxy or ethoxy group if X or Y is a methoxy group or an ethoxy group; otherwise it is hydrogen atom, The invention also covers antiartheriosclerotic, antihyperlipoproteinemic pharmaceutical compositions, suitable for inhibiting the formation of thrombuses, comprising the compounds of formula I in an effective dose, a process for preparing the same and methods for the treatment of hyperlipoproteinemia with the aid of the said compounds or compositions.

10 Claims, No Drawings

ANTIHYPERLIPOPROTEINEMIC 5-BENZYL SUBSTITUTED-BENZIMIDAZOLINE-2-THION DERIVATIVES

The present invention relates to novel antihyperlipoproteinemic 5-benzyl substituted benzimidazoline-2-thion derivatives of formula I

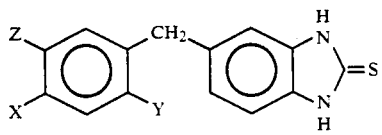 (I)

and a process for preparing the same. In formula I

X represents a halogen atom, methyl, ethyl, methoxy or ethoxy group,

Y stands for hydroxy if X is methoxy or ethoxy, otherwise it represents a hydrogen atom, methoxy or ethoxy group, Z is methoxy or ethoxy group if X or Y represents a methoxy group, or an ethoxy group, otherwise it is hydrogen atom.

The compounds of formula I can also be in tautomeric forms corresponding to formulae (Ia) or (Ib),

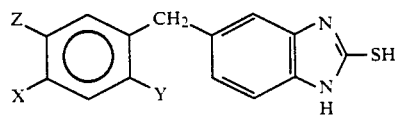 (Ia)

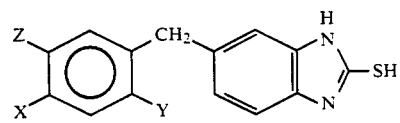 (Ib)

however, for the sake of better understanding, the compounds are referred to later on as their structure would correspond to the "thion" form according to formula I.

The invention also covers antiatheriasclerotic, antihyperlipoproteinemic pharmaceutical compositions, suitable for inhibiting the formation of thrombuses, comprising the compounds of formula I in an effective dose, a process for preparing the same and methods for the treatment of hyperlipoproteinemia with the aid of the compounds or compositions.

Atherosclerosis is a slowly progrediading process which main characteristic feature is the accumulation of lipid components of plasma, such as cholesterol esters, in the lesions of the vascular wall. The process is induced by the lesion of the endothelic portion of vascular wall. The platelets adhere to the site of lesion and variable substances liberate therefrom which induce the proliferation of the smooth muscle cells of the vascular wall.

In 1984 the experts agreed that the reason for the coronary diseases in addition to such risk factors like high blood pressure, smoking, diabetes, mainly is the high level of serum cholesterol (Consensus Development Conference: JAMA 1985, 253, 2080-2086). As the increase of serum cholesterol of the majority of the patients does not occur alone, it was suggested to maintain the serum cholesterol at a level of 200 mg/dl (National Cholesterol Education Program Expert Panel on Detection, Evaluation and Treatment of High Blood Cholesterol in Adults: Arch. Intern. Med., 1988, 148, 36-39).

Cholesterol circulates in blood bound to lipoproteins. From this point of view the LDL (low density lipoprotein) fraction is especially important as it carries the 60 to 75% of cholesterol and therefore it is the most dangerous component. Thus the reduction of this component is especially desired.

The LDL cholesterol level is to be reduced to 130 to 160 mg/dl depending on the different risk factors.

These are very strict provisions which can be satisfied only by pharmaceutical treatment. Due to this reason the demand for the blood cholesterol lowering drugs has increased. As the aim is not only the reduction of cholesterol level, but also the advantageous change of the ratio of the lipoprotein fractions carrying cholesterol, in addition to the new and fashionable, biosynthesis inhibiting drugs there is a great need for pharmaceuticals which not only reduce the total cholesterol and LDL-cholesterol levels, but also exhibit a HDL (high density lipoprotein with the protective effectiveness) fraction increasing effect.

On the basis of the recent results it is desirable that the triglycerol level, regarded as an independent risk factor, should also be reduced.

Among the blood cholesterol and triglyceride reducing agents, some aryloxy alkanecarboxylic acids were also used in therapy, from which Clofibrat (2-4-chlorophenoxy-2-methylpropionic acid ethylester) can be considered the pioneer drug. Compounds of similar structure were also launched, but regarding their chemical structure, these compounds are highly different.

Benzimidazole compounds similar to the compounds of the present invention are disclosed in Hungarian patent specification No. 193,951. These sulfur-containing benzimidazole derivatives differ from the compounds of the present invention in the substituents of the 2- and 5 positions. I.e. position 2 of the prior act compounds is substituted by a substituent of —S-alkyl type, while the same position is substituted by =S in the compounds of the present invention. The other difference is that position 5 of the compounds of the invention is substituted by an aromatic ring-substituted benzyl group.

As a result of these differences the activity of the compounds of the invention have also increased as it is shown by the results of the pharmacological tests.

The compounds of the present invention are prepared by reacting a 1,2-diamino benzene derivative of formula II

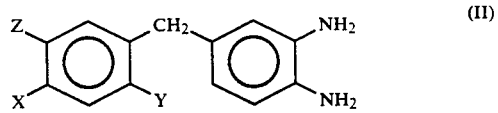 (II)

wherein X, Y and Z are the same as defined for formula I, with a thiocarbonic acid derivative of formula III

 (III)

wherein

V and W independently represent chlorine atom or amino group, or

V represents a group of formula —me—S—, wherein me stands for an alkali metal atom, then W is a methoxy or ethoxy group, or V and W together represent a further sulfur atom or they individually stand for a 1-imidazolyl group.

It is especially preferable to react a compound of formula II with a compound of formula III, wherein V represents a group of formula me—S— and W is methoxy or ethoxy group. Such compound may be e.g. potassium ethylxanthogenate, which is a stable, solid substance. The synthesis itself can be carried out as described in Org. Synth. Coll. Vol. 4, 569 (1963).

The synthesis of 3,4-diamino benzophenone is known from the prior art, though the diamino benzophenones carrying the substituents as defined hereinabove, represented by X, Y and Z, are novel compounds.

The pharmaceutical compositions comprising the compounds of formula I and the process for the preparation thereof, also belong to the present invention. The compositions are prepared by mixing one or more compounds of formula I with a suitable amount of one or more, pharmaceutically acceptable carriers, diluents, stabilizing agents, flavorants, ordorants, solvents, wetting agents, surface active agents, auxiliary substances and forming a pharmaceutical formulation preferably comprising 20 to 500 mg of active substances.

The effectiveness of the compounds of the present invention was tested as follows:

TEST METHODS

Hannover-Wistar rats weighing 140 to 160 g were fed with a LATI rat food comprising 1.5% of cholesterol and 0.5% of sodium cholate for 7 days (Schurr, P. E., Schultz, J. R., Day, C. E.: Atherosclerosis Drug Discovery, Ed.: C. E. Day; Plenum Press, New York, 215 (1976)).

Due to the effect of the fodder, the blood cholesterol level of the animals increased by 200 to 250%, while the HDL blood cholesterol level thereof was reduced by 50%.

Groups containing 6 animals each were formed. The treatments with the compounds of the invention were started on the 4th day of the addition of the cholesterol fodder and continued by the end of the test. The suspension of the compounds was administered orally. After finishing the treatment, the animals were starved for 18 hours, deblooded in narcosis with ether and the serum total cholesterol, triglyceride, LDL+VLDL and HDL cholesterol were measured.

The serum total cholesterol, HDL cholesterol and triglyceride were measured by using Beckman enzyme tests. The measuring of LDL+VLDL was carried by turbidimetric method after heparine-manganese treatment (Schurr, P. E., Schultz, J. R., Day, C. E.: Atherosclerosis Drug Discovery; Ed. C. E. Day, Plenum Press, New York, 215 (1976)).

The mechanism of action of compound according to Example 3 (further on: RGH-4819), which proved to be the best, was also tested. The tests were carried out by using rats made hyperlididemic by Triton WR-1339 (octylphenol polyethylene glycol ether/formaldehyde, product of Serva Feinbiochemica Gmbh. et Co, Heidelberg, Germany).

The animals were orally administered with the appropriate dose of the compounds for 10 days, then they were intravenously treated with Triton 6 hours before slaughtering. Due to the effect of Triton WR-1339, the level of serum cholesterol increased to 1.5-fold of the original one, while the serum triglyceride level elevated from the normal 60 to 70 mg/dl to 800 to 1500 mg/dl.

In the 6 hour test the cholesterol level increased as a result of the advanced biosynthesis. In this period the inhibition of cholesterol biosynthesis can be indirectly estimated. The high triglyceride values derive from the inhibited decomposition process, i.e. the surface active Triton WR-1339 inhibits the operation of lipoprotein lipase playing a role in the catabolism of triglycerides.

In the tests the closest structural analogue known from the prior art (Hungarian patent specification No. 193,951), 5-benzyl-2-(2-propenylthio)-benzimidazole hydrochloride (further on compound No. 0202479) was used as comparative compound.

The results are summarized in Tables 1, 2 and 3. In Table 1 the results of the screening test carried out on rats fed with cholesterol are summarized. Table 2 shows the dose-response relations on the basis of a ten-day test carried out on rats fed by cholesterol. Table 3 comprises the data relating to the mechanism of action obtained by using rats made hyperlipidemic by administering Triton WR-1339.

In the short-term tests (feeding with cholesterol for 7 days, treatment for 4 days) the compounds of the invention have shown extremely good blood cholesterol reducing effect. They significantly reduced the triglyceride and LDL+VLDL levels. The compounds exerted variable activity for changing the level of the protective HDL-cholesterol level.

The results of the dose-response tests (Table 2) show that the compound of the present invention reduced the serum cholesterol level in case-related manner. Similarly a good result was obtained in the case of the atherogenic LDL+VLDL fraction. The amount of the protective HDL-fraction has also slightly increased. The reduction of the triglyceride level was less. These effects were higher than that of the comparative compound.

The data relating to the mechanism of action of rats made hyperlipidemic by Triton WR-1339 (Table 3) verify that the compound of the invention is more effective than the comparative compound. The higher activity was mainly indicated by the reduction of the serum triglyceride level, but the reduction of the cholesterol level was dose-dependent.

This test indirectly shows that the active ingredient inhibits either the biosynthesis or the adsorption of cholesterol. The reduction of triglyceride level may be attributed to the fact that the active ingredient activates the lipoprotein lipase enzyme, having a very important role in the decomposition of triglycerides, and which activity is inhibited by Triton.

TABLE 1

Lipid reducing activities measured on rats fed by cholesterol (cholesterol feeding: 7 days, treatment: 4 days)

| Compound (example) | Dose mg/kg | cholesterol | Serum triglyceride | LDL + VLDL | HDL-cholesterol |
|---|---|---|---|---|---|
| | | | change in % | | |
| 2. | 30.0 | −22.3 | −22.9 | −35.4 | 40.6 |
| 3. | 30.0 | −39.7 | −35.7 | −73.6 | 15.1 |
| 8. | 30.0 | −34.6 | 0.0 | −45.3 | 64.3 |
| 1. | 30.0 | −26.1 | 0.0 | −38.3 | −20.8 |
| 7. | 30.0 | −36.2 | −64.5 | −36.1 | 16.7 |
| 9. | 30.0 | −43.5 | −43.2 | −53.5 | 2.0 |
| 10. | 30.0 | −33.0 | −33.0 | −33.9 | −7.6 |
| 0202479 | 30.0 | −36.5 | −22.3 | −50.2 | −24.6 |

TABLE 2

The effect of RGH-4819 on rats fed by cholesterol
(ten-day experiment)

| Compound (example) | Dose mg/kg | cholesterol | Serum triglyceride | LDL + VLDL | HDL-cholesterol |
|---|---|---|---|---|---|
| | | | change in % | | |
| 3. | 1.0 | −4.4 | 23.5 | −21.7 | 4.9 |
| 3. | 3.0 | −33.1$^{xx}$ | −14.8 | −45.8$^{xx}$ | 0.5 |
| 3. | 10.0 | −53.8$^{xx}$ | −28.5$^x$ | −72.7$^{xx}$ | 18.6$^x$ |
| 3. | 30.0 | −46.5$^{xx}$ | −18.4 | −68.7$^{xx}$ | 16.6 |
| 0202479 | 3.0 | −3.6 | −1.4 | −15.9 | 9.4 |
| 0202479 | 10.0 | −13.2 | −13.0 | −28.1$^x$ | 10.5 |
| 0202479 | 30.0 | −36.5$^{xx}$ | −22.3 | −50.2$^{xx}$ | 24.6$^x$ |

TABLE 3

The effect of RGH-4819 to rats treated by Triton WR-1339
(Triton lipemia after 6 hours)

| Compound (example) | Dose mg/kg | cholesterol | Serum triglyceride |
|---|---|---|---|
| | | change in % | |
| 3. | 10.0 | −19.4 | −36.0$^{xx}$ |
| 3. | 3.0 | −24.9 | −40.7$^{xx}$ |
| 3. | 100.0 | −28.7 | −48.5$^{xx}$ |
| 0202479 | 30.0 | −20.4 | −19.1 |
| 0202479 | 100.0 | −25.2 | −18.2 |

$^x = 0.01 \leq P \leq 0.05$;
$^{xx} = P \leq 0.01$

The invention is further illustrated by the following, non-limiting examples.

EXAMPLE 1

5-[(4-Chlorophenyl)-methyl]-2,3-dihydro-1H-benzimidazole-2-thione 6.54 g (99 mmoles) of 85% solid potassium hydroxide are dissolved in a mixture of 40 ml of ethanol and 18 ml of water, then 13.75 g (45 mmoles) of 4-[(4-chlorophenyl)-methyl]-o-phenylene-diamine dihydrochloride are added and the mixture is stirred at a temperature of 60° C. until a homogenous solution is obtained (for about 5 minutes).

Then 8.65 g (54 mmoles) of O-ethyl-S-potassium-dithiocarbonate are added to the solution and the solution is boiled for 9 hours. The reaction mixture is poured into 400 ml of water and acidified by acetic acid (about 10 ml) added in small portions under constant stirring.

The suspension thus obtained is stirred for a further 1 hour, the product is filtered off, then washed sulfide-free with 5×80 ml of water. The wet substance filtered through a vacuum filter, is recrystallized from t-butanol after clarifying the same with charcoal.

Yield: 10.3 g (83%).
Melting point: 275°-280° C.

EXAMPLE 2

5-[(4-Methylphenyl)-methyl]-2,3-dihydro-1H-benzimidazole-2-thione

The title product is obtained by starting from 12.83 g (45 mmoles) of 4-[(4-methylphenyl)-methyl]-o-phenylene-diamine dihydrochloride under the same reaction conditions and by using the reagents in the same molar rate as described in Example 1. The crude product is crystallized from n-butanol.

Yield: 9.77 g (85%).
Melting point: 258°-260° C.

EXAMPLE 3

5-[(4-Methoxyphenyl)-methyl]-2,3-dihydro-1H-benzimidazole-2-thione 1.15 g (17 mmoles) of 85% solid potassium hydroxide are dissolved in a mixture of 70 ml of ethanol and 23 ml of water. Then 19.00 g (83.2 mmoles) of 4-[(4-methoxyphenyl)-methyl]-o-phenylene-diamine and 15.4 g (95.8 mmoles) of O-ethyl-S-potassium-dithiocarbonate are added and the reaction mixture is stirred for 9 hours.

The reaction mixture is poured into 900 ml of water. The crude product is isolated as described in Example 1. The wet substance, previously filtered through a vacuum-filter, is clarified by charcoal and crystallized from 800 ml of i-propanol.

Yield: 18.0 g (80%).
Melting point: 254°-255° C.

EXAMPLE 4

5-[(4-Methoxyphenyl)-methyl]-2,3-dihydro-1H-benzimidazole-2-thione

To a mixture of 22 ml of ethanol, 3.5 ml of water and 0.83 g (12.6 mmoles) of 85% potassium hydroxide 2.5 g (10.95 mmoles) of 4-[(4-methoxyphenyl)-methyl]-o-phenylene-diamine and 0.96 g (0.76 ml, 12.6 mmoles) of carbon disulfide are added and the mixture is refluxed for 5 hours.

Then the reaction mixture is cooled, 25 ml of water are added, then acidified by the addition of 2.80 g of 50% (23.3 mmoles) acetic acid solution under thorough stirring and external cooling with ice.

After 1 hour stirring the crude product is filtered off, washed with 3×20 ml of water and clarified by the addition of charcoal, the wet product is crystallized from 70 ml of isopropanol. Thus white, crystalline title product is obtained.

Yield: 1.64 g (55.4%).
Melting point: 254°-255° C.

EXAMPLE 5

5-[(4-Methoxyphenyl)-methyl]-2,3-dihydro-1H-benzimidazole-2-thione

A mixture of 0.35 g (1.16 mmoles) of 4-[(4-methoxyphenyl)-methyl]-o-phenylene-diamine dihydrochloride and 0.286 g (3.76 mmoles) of thiourea are melted in an oil-bath at a temperature of 150°-160° C. and kept at the same temperature for 2 hours.

The cooled reaction mixture is triturated with 10% aqueous sodium carbonate solution and the suspension is stirred for 1 hour. The crude product is filtered off, washed with water four times, then dissolved, the hot solution is treated with charcoal, then crystallized from i-propanol.

Yield: 88 mg (28%).
Melting point: 252°-254° C.

EXAMPLE 6

5-[(4-Methoxyphenyl)-methyl]-2,3-dihydro-1H-benzimidazole-2-thione

To 1.14 g (5.0 mmoles) of 4-[(4-methoxyphenyl)-methyl]-o-phenylene-diamine dissolved in 30 ml of dry tetrahydrofuran a solution of 0.98 g (5.5 mmoles) of N,N'-thiocarbonyl-imidazole and 15 ml of dry tetrahydrofuran is added dropwise under external cooling.

The reaction mixture is stirred for 5 hours at room temperature, then 1.5 ml of water are added and stirred for a further ½ hours. Then the solvent is distilled off in vacuo and the evaporation residue is treated with water. The crude product thus obtained is filtered off, washed three times with water and crystallized from i-propanol as described in Example 5.

Yield: 0.9 g (51.0%).
Melting point: 253°–255° C.

EXAMPLE 7

5-[(4-Methoxyphenyl)-methyl]-2,3-dihydro-1H-benzimidazole-2-thione

To a solution of 0.51 g (5.0 mmoles) of triethyl amine, 1.14 g (5.0 mmoles) of 4-[(4-methoxyphenyl)-methyl]-o-phenylene-diamine and 35 ml of chloroform a solution of 0.58 g (5.0 mmoles) of thiophosgene and 10 ml of chloroform are added dropwise.

The reaction mixture is stirred for 1 hour, then the solvent is removed in vacuo. The evaporation residue is triturated with 5% sodium carbonate solution and filtered after 2 hour stirring. The crude product is washed with water three times, then crystallized from i-propanol as described in Example 5.

Yield: 0.68 g (50.3%).
Melting point: 254°–255° C.

EXAMPLE 8

5-[(3,4-Dimethoxyphenyl)-methyl]-2,3-dihydro-1H-benzimidazole-2-thione

The title product is prepared by using 18.30 g (70.9 mmoles) of 4-[(3,4-dimethoxyphenyl)-methyl]-o-phenylene-diamine as starting material under the same reaction conditions and in the same molar rate of the reagents as described in Example 3. The crude product is crystallized from n-butanol.

Yield: 7.1 g (33%).
Melting point: 248°–250° C.

EXAMPLE 9

5-[(2-Hydroxy-4-methoxyphenyl)-methyl]-2,3-dihydro-1H-benzimidazole-2-thione

The title product is prepared by using 22.83 g (100 mmoles) of 4-[(2-hydroxy-4-methoxyphenyl)-methyl]-o-phenylenediamine as starting material under the same reaction conditions and in the same molar weight of the reagents as described in Example 3. The crude product is crystallized from n-butanol.

Yield: 14.0 g (49%).
Melting point: 248°–250° C.

EXAMPLE 10

5-[(4-Ethoxyphenyl)-methyl]-2,3-dihydro-1H-benzimidazole-2-thione

The title product is prepared by using 12.1 g (50.0 mmoles) of 4-[(4-ethoxyphenyl)-methyl]-o-phenylene-diamine as starting material under the same reaction conditions and in the same molar rate of the reagents as described in Example 3. The crude product is crystallized from n-butanol.

Yield: 11.6 g (82%).
Melting point: 243°–246° C.

EXAMPLE 11

5-[(2,5-Dimethoxyphenyl)-methyl]-2,3-dihydro-1H-benzimidazole-2-thione

The title product is prepared by using 18.30 g (70.9 mmoles) of 4-[(2,5-dimethoxyphenyl)-methyl]-o-phenylene-diamine as starting material under the same reaction conditions and in the same molar rate of the reagents as described in Example 3. The crude product is crystallized from n-butanol.

Yield: 15.5 g (73%).
Melting point: 210°–211° C.

EXAMPLE 12

Preparation of tablets comprising 30 mg of active ingredient

Engraved-edged tablets of a diameter of 9 mm and a weight of 250 mg are prepared according to the known tabletting method. The composition of the tablets is as follows:

| | |
|---|---|
| 5-[(4-methoxyphenyl)-methyl]-2,3-dihydro-1H-benzimidazole-2-thione | 30.0 mg |
| lactose | 130.0 mg |
| starch | 64.0 mg |
| polivinyl pyrrolidone (polividone) | 5.0 mg |
| microcrystalline cellulose | 10.0 mg |
| talc | 7.5 mg |
| magnesium stearate | 2.5 mg |
| colloidal silicic acid | 1.0 mg. |

EXAMPLE 13

Capsules comprising 125 mg of active ingredient

Hard gelatine capsules of a size of No. 1 are filled with the following composition:

| | |
|---|---|
| 5-[(4-methoxyphenyl)-methyl]-2,3-dihydro-1H-benzimidazole-2-thione | 125.0 mg |
| polyvinyl pyrrolidone (polividone) | 5.0 mg |
| microcrystalline cellulose | 58.0 mg |
| talc | 6.0 mg |
| magnesium stearate | 5.0 mg |
| colloidal sillicic acid | 1.0 mg |

What is claimed is:

1. A compound of the formula I

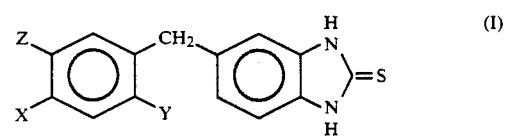

wherein
X is a halogen atom, or a methyl, ethyl, methoxy or ethoxy group,
Y is hydroxy if X is methoxy or ethoxy, otherwise Y is a hydrogen atom, or a methoxy or ethoxy group,
Z is a methoxy or ethoxy group if X or Y is a methoxy group or ethoxy group, otherwise Z is a hydrogen atom.

2. 5-[(4-Chlorophenyl)-methyl]-2,3-dihydro-1H-benzimidazole-2-thione as defined in claim 1.

3. 5-[(4-Methoxyphenyl)-methyl]-2,3-dihydro-1H-benzimidazole-2-thione as defined in claim 1.

4. 5-[(3,4-Dimethoxyphenyl)-methyl]-2,3-dihydro-1H-benzimidazole-2-thione as defined in claim 1.

5. 5-[(2-Hydroxy-4-methoxyphenyl)-methyl]-2,3-dihydro-1H-benzimidazole-2-thione as defined in claim 1.

6. 5-[(4-Ethoxyphenyl)-methyl]-2,3-dihydro-1H-benzimidazole-2-thione as defined in claim 1.

7. 5-[(2,5-Dimethoxyphenyl)-methyl]-2,3-dihydro-1H-benzimidazole-2-thione as defined in claim 1.

8. 5-[(4-Methylphenyl)-methyl]-2,3-dihydro-1H-benzimidazole-2-thione as defined in claim 1.

9. An antihyperlipoproteinemic pharmaceutical composition which comprises a pharmaceutically effective amount of the compound of the formula I, as defined in claim 1, together with a pharmaceutically acceptable inert carrier.

10. An antihyperlipoproteinemic method of treatment which comprises administering to a mammalian subject in need of said treatment a pharmaceutically effective amount of a compound of the formula I, as defined in claim 1.

* * * * *